United States Patent
Fujiwara et al.

(10) Patent No.: US 6,780,647 B2
(45) Date of Patent: Aug. 24, 2004

(54) SENSOR MATERIAL, SENSOR AND DETECTION METHOD FOR BIO-SUBSTANCE

(75) Inventors: Shoichiro Fujiwara, Minamiashigara (JP); Masato Mikami, Minamiashigara (JP); Takashi Uematsu, Minamiashigara (JP); Ryojiro Akashi, Minamiashigara (JP)

(73) Assignee: Fuji Xerox Co., Ltd., Tokyo (JP)

( * ) Notice: Subject to any disclaimer, the term of this patent is extended or adjusted under 35 U.S.C. 154(b) by 302 days.

(21) Appl. No.: 09/966,079

(22) Filed: Oct. 1, 2001

(65) Prior Publication Data

US 2002/0068019 A1 Jun. 6, 2002

(30) Foreign Application Priority Data

Dec. 6, 2000 (JP) .................................... 2000-371234

(51) Int. Cl.$^7$ .............................................. G01N 21/25
(52) U.S. Cl. ...................... 436/169; 422/56; 422/82.09
(58) Field of Search ............................. 422/55, 56, 57, 422/82.06, 82.09; 436/531, 532, 533, 534, 535, 164, 169

(56) References Cited

U.S. PATENT DOCUMENTS 5,854,078 A * 12/1998 Asher et al. ................ 436/133
6,287,485 B1 * 9/2001 Akashi et al. .............. 252/583
6,593,588 B1 * 7/2003 Reimer ........................ 250/573

FOREIGN PATENT DOCUMENTS

JP          8-201296 A          8/1996

OTHER PUBLICATIONS

S. Suzuki (Ed.), Biosensor, Tokyo, Kodansha, 1984, pp. 91–102.

E. Kokufuda, Journal of Society of Environmental Science, Japan, vol. 10, No. 2, pp. 173–187 (1997).

* cited by examiner

Primary Examiner—Jeffrey R. Snay
(74) Attorney, Agent, or Firm—Oliff & Berridge, PLC (57) ABSTRACT

Provided is a sensor material including at least a stimulus-responsive high polymer gel, a bio-substance-responsive material and a light modulation material. A sensor having at least the sensor material and an optical waveguide is also provided. Furthermore, provided are a detection method for a bio-substance using the sensor material in which a change in tone is detected on the basis of swelling or shrinking of the stimulus-responsive high polymer gel, and a detection method for transmitting light using a sensor material in which transmitting light is detected on the basis of swelling or shrinking of the stimulus-responsive high polymer gel.

9 Claims, 4 Drawing Sheets

SENSOR MATERIAL, SENSOR AND DETECTION METHOD FOR BIO-SUBSTANCE

BACKGROUND OF THE INVENTION

1. Field of the Invention

The present invention relates to a sensor material, a sensor, a detection method for a bio-substance and a detection method for transmitting light, and particularly, to a sensor material capable of reacting with various chemical materials or various bio-substances to detect an amount or the like of a material on the basis of a change in optical characteristic thereof, to a sensor, to a detection method for a bio-substance.

2. Description of the Background Art

A sensor (a biosensor) currently used for detecting a bio-substance is mainly constructed of a section producing a signal by use of a biochemical reaction and a signal converting section converting the signal to a current or the like. There have been available, as examples of such biosensors, an enzyme sensor utilizing an enzymatic reaction as a biochemical reaction, which is a biosensor for a clinical chemical analysis, an immunity sensor using an antigen or an antibody, and other sensors. An enzyme sensor is described which has a structure in which an enzyme film is fixedly mounted on a sensing surface of an electrode in S. Suzuki (Ed.), BIOSENSOR, Tokyo, Kodansha, 1984; pp. 91 to 102.

Theses biosensors have, in principle, had drawbacks that a measuring apparatus such as an ammeter is required, leading to not only high cost but also large working space required when used.

As a simple and convenient biosensor with no such drawbacks, there has been known a smell sensor, as disclosed in Japanese Published Unexamined Patent Application No. Hei 8-201296, in which an antibody against an odorant is dispersed in agar. The smell sensor detects a smell on the basis of a change in light transmittance in the agar due to agglomerates of the antibody and the odorant produced through an interaction therebetween.

Further, as materials that are expected to be utilized as a biosensor according to a nature selectively responding to a specific bio-substance, there are named materials each including a bio-substance-response material in a stimulus-responsive high polymer. As an example thereof, there has been known a chemo-mechanical material formed by entrapping glucose oxidase and urease in network high polymer chains obtained by cross-linking a co-polymer constituted of N-isopropyl acrylamide (see E. Kokufuda, journal of Society of Environmental Science, Japan, Vol. 10, No. 2, pp. 173–187 (1997)). This material has a property that it shrinks by addition of glucose while swelling by addition of urea.

The smell sensor and the chemo-mechanical material responding to a bio-substance have various problems on which improvement is to be performed in order to utilize them as biosensors.

A smell sensor disclosed in Japanese Published Unexamined Patent Application No. Hei 8-201296 detects a smell only on the basis of a change in transmittance caused by agglomerates of an antibody and an odorant; therefore, its sensitivity is so poor that difficulty has occurred in quantification of a concentration of the odorant.

Furthermore, while a chemo-mechanical material can be adapted to more of various bio-material-responsive materials than can a smell sensor, a change in volume is hard to be visually recognized in a case where it is used as a simple and easy biosensor like a smell sensor, resulting in a problem of difficulty in quantification of a concentration of a bio-substance.

SUMMARY OF THE INVENTION

The present invention has been made in view of above circumstances and provides a sensor material that requires no measuring apparatus having been required mainly for a biosensor, when used in a sensor, the sensor being capable of being utilized as a low-cost, simple and easy sensor, being more suited for quantification of a concentration of a bio-substance than is a smell sensor and being further capable of detecting various bio-substances, the sensor and a detection method for a bio-substance, all using the sensor material.

The present invention has been made in view of the above circumstances and will be shown below. That is, one aspect of the present invention is directed to a sensor material including at least a stimulus-responsive high polymer gel, a bio-substance-responsive material and a light modulation material.

Another aspect of the present invention is directed to a sensor material, in which at least the bio-substance-responsive material and the light modulation material are present inside the stimulus-responsive high polymer gel.

Another aspect of the present invention is directed to a sensor material, in which the light modulation material is present inside the stimulus-responsive high polymer gel while the bio-substance-responsive material is present outside the stimulus-responsive high polymer gel.

Another aspect of the present invention is directed to a sensor material, in which the stimulus-responsive high polymer gel swells or shrinks according to a concentration of the bio-substance.

Another aspect of the present invention is directed to a sensor material, in which a concentration of the light modulation material included in the stimulus-responsive high polymer gel is equal to or higher than a saturated absorption concentration or a saturated scattering concentration when the stimulus-responsive high polymer gel shrinks.

Another aspect of the present invention is directed to a sensor material, in which a ratio of a volume of the stimulus-responsive high polymer gel when in swelling to a volume of the stimulus-responsive high polymer gel when in shrinking is 5 or more.

Another aspect of the present invention is directed to a sensor having at least one of the above sensor materials and an optical waveguide.

Another aspect of the present invention is directed to a detection method for a bio-substance using one of the above sensor materials, in which a change in tone is detected on the basis of swelling or shrinking of the stimulus-responsive high polymer gel.

Another aspect of the present invention is directed to a detection method using the stimulus-responsive high polymer gel for detecting a bio-substance, in which a transmitting light therethrough is detected on the basis of swelling or shrinking of the stimulus-responsive high polymer gel.

BRIEF DESCRIPTION OF THE DRAWINGS

Preferred embodiments of the present invention will be described in detail based on the followings, wherein:

FIGS. 1A and 1B are pictorial and schematic representations describing an example of a configuration of a sensor material of the present invention and a principle of operation thereof, wherein FIG. 1A shows a swollen and colored state of the sensor material and FIG. 1B shows a shrunk and decolored state of the sensor material;

FIGS. 2A and 2B are pictorial and schematic representations showing an example of a detection method for a bio-substance using a sensor material of the present invention, wherein FIG. 2A shows a contacted state of the sensor material and FIG. 2B shows a swollen state of the sensor material;

FIGS. 3A and 3B are pictorial and schematic diagrams showing an example of a sensor of the present invention, wherein FIG. 3A shows a shrunk state of the sensor material and FIG. 3B shows a swollen state of the sensor material; and FIGS. 4A and 4B are pictorial and schematic diagrams showing an example of a sensor of the present invention, wherein FIG. 4A shows a shrunk state of the sensor material and FIG. 4B shows a swollen state of the sensor material.

DESCRIPTION OF THE PREFERRED EMBODIMENTS

A description will be given of a sensor material of the present invention and a sensor using the sensor material, and in addition, a detection method for a bio-material and a detection method for transmitting light as well.

Sensor Material

A sensor material of the present invention indispensably includes at least a stimulus-responsive high polymer gel, a bio-substance-responsive material reacting with a bio-substance and a light modulation material and it is preferable that at least the light modulation material is present inside the stimulus-responsive high polymer gel and further that the bio-substance-responsive material is present outside or inside the stimulus-responsive high polymer gel.

A sensor material of the present invention works such a way that a bio-substance-responsive material (for example, enzyme or the like) present inside or outside a stimulus-responsive high polymer gel reacts with a bio-substance to be detected and pH, a chemical material concentration and others inside or outside the stimulus-responsive high polymer gel change, whereby a change in volume of the stimulus-responsive high polymer occurs. A color of the sensor material changes in company with the change in volume.

Figure 1A:
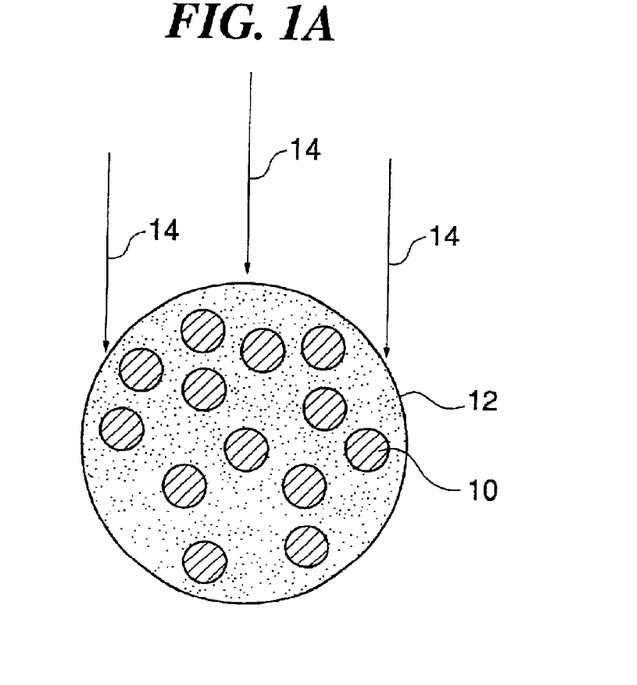
Figure 1B:
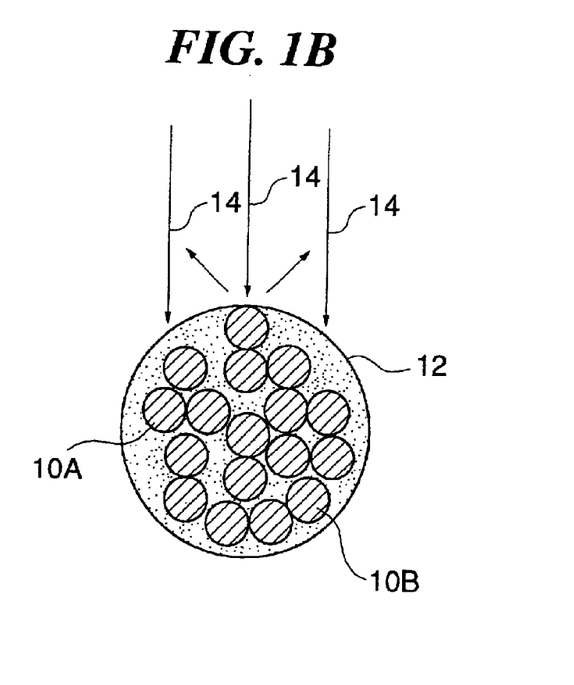

In FIGS. 1A and 1B, there are shown a concrete example of a configuration of a sensor material of the present invention and a principle of operation thereof.

FIG. 1A shows a sensor material of the present invention in a colored state (a swollen state) as being in a particulate state. A light modulation material 10, as shown in FIG. 1A, is preferably diffused or dispersed in a uniform manner in a liquid swelling mass of a stimulus-responsive high polymer gel 12 including a bio-substance-responsive material, which is a component material. With the uniform diffusion and dispersion, the light modulation material 10 effectively absorbs or scatters light 14, thereby increasing a light absorption efficiency or light scattering efficiency of the sensor material.

FIG. 1B shows a sensor material of the present invention in a decolored state (a shrunk state) as being in a particulate state. The stimulus-responsive high polymer gel 12, as shown in FIG. 1B, shrinks to reduce an area in which light is absorbed or scattered and thereby, decrease an absorbed light amount or a scattered light amount. A density of the light modulation material 10 is increased into agglomerates by shrinking of the stimulus-responsive high polymer gel 12. Thereby, a concentration of the light modulation material increases to equal to or higher than a saturated absorption concentration or saturated scattering concentration to reduce an absorbed light amount or light scattering amount per unit amount of the light modulation material and as a result, decrease a light absorption efficiency or light scattering efficiency of a sensor material.

This is considered such that when the light modulation material 10 is agglomerated to form agglomerates of a size or larger, the light modulation material 10A present on the surfaces of (outside) the agglomerates absorb or scatter light while the light modulation material 10B present in the interior of (inside) the agglomerates comes not to participate in absorption or scattering of light, so reduction occurs in an absorbed light amount or scattered light amount per unit amount of the light modulation material 10.

Furthermore, it has also been known that when the stimulus-responsive high polymer gel 12 shrinks, a non-uniform structure is formed in the gel 12 to increase a degree of light scattering compared with when in swelling and especially, it is therefore considered that by light scattering on the surface of the stimulus-responsive high polymer gel 12, there is also exerted an action that reduction occurs in a light absorbing ability and a color purity of the light modulation material 10. It is totally considered that the actions are combined to produce a great difference in absorbed light amount between when in swelling and when in shrinking of the stimulus-responsive high polymer gel 12, resulting in a change in coloration density. That is, a coloration density can be controlled in various ways by a change in volume of a material constituted of the stimulus-responsive high polymer gel 12 including the light modulation material 10. In addition, it is possible to change a volume of the stimulus-responsive high polymer gel 12 stepwise, which in turn makes it possible to produce a half tone color in optical density.

It is preferable that a stimulus-responsive high polymer gel 12 is stimulus responsive such that absorption or release of liquid is caused by various kinds of stimulus such as a change in pH caused by an enzymatic reaction or the like reaction, a change in ion concentration, absorption or adsorption of a chemical material, a change in solvent composition or others, which in turn leads to a reversible change in volume (swelling or shrinking).

To be concrete, a stimulus-responsive high polymer gel 12 being stimulus-responsive to a change in pH caused by an enzymatic reaction or the like is preferably a high polymer gel electrolyte and there can be named: a cross-linked poly(meth)acrylic acid and a salt of the cross-linked product; cross-linked copolymers of (meth)acrylic acid with at least one selected from the group of (meth)acrylamide, hydroxyethyl (meth)acrylate, (meth)acrylic acid alkylester and others, and a salt of each cross-linked product; cross-linked copolymers of maleic acid with at least one selected from the group of (meth)acrylamide, hydroxyethyl (meth)acrylate, (meth)acrylic acid alkylester and others, and a salt of each cross-linked product; cross-linked polyvinylsulfonic acid or cross-linked copolymers of vinylsulfonic acid with at least one selected from the group of (meth)acrylamide, hydroxyethyl (meth)acrylate, (meth)acrylic acid alkylester and others, and a salt of each cross-linked product; cross-linked polyvinylbenzenesulfonic acid and a salt of the cross cross-linked product; cross-linked copolymers of vinylbenzenesulfonic acid with at least one selected from the group of (meth)acrylamide, hydroxyethyl (meth)acrylate, (meth)acrylic acid alkylester and others, and a salt of each cross-linked product; cross-linked polyacrylamide alkylsulfonic acid and a salt of the cross-linked product; cross-linked copolymers of acrylamide alkylsulfonic acid with at least one selected from the group of (meth)acrylamide, hydroxyethyl (meth)acrylate, (meth)acrylic acid alkylester and others, and a salt of each cross-linked product; cross-linked polydimethylaminopropyl(meth)acrylamide and a salt of the cross-linked product; cross-linked copolymers of dimethylaminopropyl(meth)acrylamide with at least one selected from the group of (meth)acrylic acid, (meth) acrylamide, hydroxyethyl (meth)acrylate, (meth)acrylic acid alkylester and others, and a salt of each cross-linked product; a cross-linked composite of polydimethylaminopropyl (meth)acrylamid and polyvinylalcohol and a salt of the cross-linked composite; a cross-linked composite of polyvinyl alcohol and poly(meth)acrylic acid and a salt of the cross-liked composite; cross-linked carboxyalkyl-cellulose salt; a partial hydrolyzate of cross-linked poly(meth) acrylonitril and a salt of the cross-linked product; and others, wherein the term (meth)acrylic means both of (meth)acrylic and acrylic.

A stimulus-responsive high polymer gel 12 being stimulus-responsive to a change in solvent composition and a change in ion concentration is preferably one whose change in volume is large and the above-described high polymer electrolyte gels are exemplified as such stimulus-responsive high polymers 12.

An amount of a change in volume of a stimulus-responsive high polymer gel 12 is preferably large and a ratio of a volume when in swelling to one when in shrinking is 5 or more, more preferably 10 or more, and further more preferably 15 or more. If the volume ratio is less than 5, there is a chance that a light modulation contrast is insufficient to result in making an indicating color unclear.

While there is no specific limitation on a bio-substance with which a bio-substance-responsive material reacts, there can be named, to be concrete: saccharides or polysaccharides such as glucose, sucrose, maltose, galactose and others; cholesterols including cholesterol and cholesterol ester; phosphatidylcholine, neutral lipid, urea, uric acid, lactic acid, oxalic acid, pyruvic acid, ascorbic acid, amino acid, alcohol, creatinine, adenosine, adenosine-5'-monophosphate, adenosine-5'-triphosphate, amygdalin, penicillin, monoamine, enzymes, DNA (deoxyribonucleic acid), RNA (ribonucleic acid), inorganic salts, proteins, histamine, iron components and others.

A bio-substance-responsive material is preferably one performing a biochemical reaction so as to swell or contract a stimulus-responsive high polymer 12 by reacting with a bio-substance as described above, whose molecular structure has no specific limitation thereon.

To be concrete, as bio-substance-responsive materials, there are named enzyme, DNA, RNA, chelate, proteins and others and among them, the followings are preferably used: glucose oxidase, glucose amylase, galactose oxidase, tyrosinase, catechol 1,2-oxygenase, pyruvic acid oxidase, D- or L-amino acid oxidase, amine oxidase, cholesterol oxidase, cholesterol esterase, choline oxidase, alcohol dehydrogenase, glutamic acid dehydrogenase, glutaminase, asparaginase, cholesterol dehydrogenase, aldehyde dehydrogenase, glucose dehydrogenase, fructose dehydrogenase, sorbitol dehydrogenase, glycerol dehydrogenase, peroxidase, invertase, mutarotase, glucoamylase, phospholipase, L-lisine carboxylase, L-phenylalanine ammonia lyase, L-methionine ammonia lyase, D-choline oxidase, lipase, phospholipase, lipoprotein lipase, diaphorase, urease, uricase, lactic acid oxidase, lactic acid dehydrogenase, oxalic acid decarboxylase, oxalic oxidase, ascorbic acid oxidase, amino acid oxidase, decarboxylase, ammonia lyase, alcohol oxidase, creatinase, catalase, phosphatase, nitrate reductase, nitrite reductase, arylsulfatase, adenosine deaminase, AMP deaminase, hexokinase, β glucosidase, penicillinase, monoamine oxidase, L-lactic acid dehdrogenase, malic acid dehydrogenase, glyceraldehyde 3-phosphoric acid dehydrogenase, glutamate dehydrogenase, L-tyrosine decrboxylase and others.

Furthermore, it is preferable that amidoadenine dinucleotide (NAD), nicotinamideadenine dinucleotide phosphate (NADP) or the like is present as a coenzyme inside or outside a stimulus-responsive high polymer gel 12 as a catalyst for a reaction between a bio-substance and an enzyme according to a kind of enzyme.

Furthermore, it is preferable that platinum, palladium or the like, which is a catalyst initiating an oxidation-reduction reaction, is present as a coenzyme inside or outside a stimulus-responsive high polymer gel 12. At this time, by use of a pigment having metal phthalocyanine ring together with the metal catalyst, an oxidation-reduction reaction that an enzyme performs in vivo can be reproduced in vitro, which makes it possible to use the pigment as a bio-substance-responsive material of a sensor material.

As a way of inclusion of a bio-substance-responsive material inside a stimulus-responsive high polymer gel 12, there can be named methods: chemical bonding, adsorption, entrapping and others. A further method may be adopted in which a bio-substance-response material is sealed in microcapsules and the microcapsules are dispersed in the stimulus-responsive high polymer gel.

A stimulus-responsive high polymer gel 12 of the present invention preferably includes at least a light modulation material 10. As the light modulation material 10, there can be used many of publicly known pigments, dyes and light scattering materials.

As concrete examples preferably used as pigments, there can be named: bronze powder, carbon black, titanium black, anthraquinone based pigment, azo based pigment, phthalocyanine based pigment, quinacridone based pigment, perylene based pigment, indigo based pigment and others and among them, pigments with a high light absorption coefficient are especially preferable. A preferable particle size of pigment is preferably in the range of from 0.005 to 1 $\mu$m and especially preferably from 0.01 to 0.5 $\mu$m in volume average particle diameter of primary particles. When the volume average particle diameter is less than 0.005 $\mu$m, flowing out of a stimulus-responsive high polymer gel 12 is easy to occur and on the other hand, when the volume average particle diameter exceeds 1 $\mu$m, a risk occurs that a coloration density decreases.

Preferably used ones of the pigments are ones each of which has a polar group such as acidic groups including a carboxylic group and sulfonic group; a hydroxyl group; amino group; thiol group; halogen; nitro group; or a carbonyl group, in a molecule and has a characteristic that when a concentration of a pigment is high inside a stimulus-responsive high polymer gel 12, the pigment forms agglomerates with ease.

It is preferable that a pigment is contained inside a stimulus-responsive high polymer gel 12 without flowing out of the polymer gel 12. In order to prevent a pigment inside the stimulus-responsive high polymer gel 12 from flowing out, a contrivance is only required to be applied that a pigment in use has a particle diameter larger than any of interstices that a stimulus-responsive high polymer gel 12 has therein, that a pigment in use has a high interaction thereof with the stimulus-high polymer gel 12, electrically, in an ionic state and in other physical aspects, or that a pigment in use has a chemically modified surface. As pigments whose surfaces are chemically modified, there can be exemplified: a pigment on whose surface there is provided a group chemically bonding with a stimulus-responsive high polymer gel 12 and a pigment to which a stimulus-responsive high polymer gel is grafted.

As examples of preferable dyes, there can be named various dyes such as an azo dye, an anthraquinone dye, an indigo dye, a phthalocyanine dye, a carbonium dye, a quinonimine dye, a methin dye, a quinoline dye, a nitro dye, a benzoquinone dye, a naphthoquinone dye, a naphthalimide dye, a perinone and others and among them, dyes with a high optical absorption coefficient are especially preferable. Furthermore, since a dye is preferably contained inside a stimulus-responsive high polymer gel 12 without flowing out thereof, a reactive dye is especially preferred into which there is introduced a group chemically boding with a stimulus-responsive high polymer gel 12 and the like.

A concentration of a light modulation material (a colorant such as a pigment or a dye) contained in a stimulus-responsive high polymer gel 12 is preferably one which becomes, at the lowest, equal to or higher than a saturated absorption concentration when in shrinking of the stimulus-responsive high polymer gel 12.

Herein, a concentration equal to or higher than a saturated absorption concentration is a concentration at which a light absorption efficiency per unit amount of a colorant decreases in a state of a sufficiently high concentration of the colorant. Further, another way of definition of a colorant concentration equal to or higher than a saturated absorption concentration goes this way: a colorant concentration at which a relationship between a colorant concentration and an absorbed light amount under a condition of a specific optical path is largely deviated from a linear relationship.

In order to achieve a state of such a concentration equal to or higher than a saturated absorption concentration when in shrinking of a stimulus-response high polymer gel 12, it is generally required that a colorant is included in a stimulus-responsive high polymer gel 12 at a concentration of 3% by wt of a total weight of the stimulus-responsive high polymer gel 12 in a dry state, although the concentration is dependent on a particle diameter, a refractive index, a absorption coefficient, a specific weight and others of the colorant. On the other hand, when the concentration of the colorant exceeds 95% by wt, the stimulus-responsive high polymer gel 12 becomes hard to swell or shrink in good responsibility, resulting in poor responding characteristic in a case. Therefore, generally, a concentration of a colorant included in a stimulus-responsive high polymer gel 12 is preferably in the range of from 3 to 95% by wt and more preferably in the range of from 10 to 95% by wt, both, of a total weight of the stimulus-responsive high polymer gel 12 in a dry state.

Moreover, a colorant may be included in a stimulus-responsive high polymer 12 in such a way that although a concentration of a colorant included in a stimulus-responsive high polymer gel 12 in a dry state is equal to or lower than a saturated absorption concentration, a colorant concentration equal to or higher than the saturated absorption concentration can be realized locally in an agglomerated portion when the stimulus-responsive high polymer gel 12 is shrunk and the colorant is locally collected into the agglomerated portion.

While a light scattering material included in a stimulus-responsive high polymer gel 12 is preferably a material having a refractive index different from a refractive index of a liquid participating in a change in volume of the stimulus-responsive high polymer gel 12, there is no other specific limitation thereon and, for example, various kinds of inorganic materials and organic materials can each be a candidate therefor.

As concrete examples of preferable inorganic materials, there can be named: inorganic oxides such as zinc oxide, basic carbonate white lead, basic sulfate white carbonate, lead sulfate, lithopone, muscovite, zinc sulfide, titanium oxide, titanium oxynitride, antiminy oxide, lead white, zirconia, alumina, micanite, micalex, quartz, calcium carbonate, gypsum, clay, silica, diatomaceous earth, talc, basic magnesium carbonate, alumina white, gloss white, satine white; metal materials such as zinc, alumel, antimony, aluminum, aluminum alloy, iridium, indium, osmium, chromium, chromel, cobalt, zirconium, stainless steel, gold, silver, German silver, copper, bronze, tin, tungsten, tungsten steel, iron, lead, nickel, nickel alloy, nickelin, platinum, platinum-rhodium, tantalum, drumlin, nichrome, titanium, Krupp-austenite steel, constantan, brass, platinum-iridium, palladium, palladium alloy, molybdenum, molybdenum steel, manganese, manganese alloy, rhodium, rhodium alloy and others; and inorganic conductive materials such as ITO (indium-tin oxide) and others.

Furthermore, as concrete examples of a preferable organic material, there can be named: high polymer materials, such as phenol resin, fran resin, xylene-formaldehyde resin, urea resin, melamine resin, aniline resin, alkyd resin, unsaturated polyester, epoxy resin, polyethylene, polypropylene, polystyrene, poly-p-xylylene, polyvinyl acetate, acrylic resin, methacrylic resin, polyvinyl chloride, polyvinylidene chloride, fluoroplastic, polyacrylonitrile, polyvinyl ether, polyvinyl ketone, polyether, polycarbonate, thermoplastic polyester, polyamide, diene-plastics, polyurethane plastics, polyphenylene, polyphenylene oxide, polysulfone, aromatic heterocyclic polymer, silicone, natural rubber plastics and cellulose plastics; and blended materials of two or more kinds of the high polymer materials (polymer blends).

Furthermore, as the light scattering materials, there can be adopted materials used as a stimulus-responsive high polymer gel 12. No specific limitation is imposed on the light scattering materials, various kinds of high polymer resins can be used as the materials. As concrete examples of preferable high polymer resins, the above-described examples can be named in cases where the light scattering materials are of organic materials.

Moreover, shapes of light scattering materials in use has no specific limitation thereon but can be of various kinds such as particles, blocks, films and fibers, including a material of no specific shape. Among them, a particulate state is especially preferable because of features of a high light scattering property, a wide application range and others. No further limitation is imposed on particular shapes of a particle; applicable candidates are shapes of various kinds, such as a sphere, a cube, an ellipsoid, a polyhedron, a porous particle, a star-like particle, a needle-like particle, a hollow particle and a scaly particle. In a case of a particle, a volume average diameter thereof is preferably in the range of from 0.01 to 500 $\mu$m and more preferably from 0.05 to 100 $\mu$m. If the volume average diameter is less than 0.01 $\mu$m or exceeds 500 $\mu$m, a chance arises that a light scattering effect required from a light scattering material decreases. Furthermore, if the volume average diameter is less than 0.01 $\mu$m, a light scattering material is easy to flow from the interior of a stimulus-responsive high polymer gel 12.

In addition, the particles of various kinds can be produced by means of a generally applied physical or chemical pulverizing method.

Preferably used ones of the light scattering materials are ones each of which has a polar group such as acidic groups including a carboxylic group and sulfonic group; a hydroxyl group; amino group; thiol group; halogen; nitro group; or carbonyl group, in a molecule and has a characteristic that when a concentration of a light scattering material is high inside a stimulus-responsive high polymer gel 12, the material forms agglomerates with ease.

It is preferable that a light scattering material is contained inside a stimulus-responsive high polymer gel 12 without flowing out of the polymer gel 12. In order to prevent a light scattering material inside the stimulus-responsive high polymer gel 12 from flowing out, a contrivance is only required to be applied that a light scattering material in use has a particle diameter larger than any of interstices that a stimulus-responsive high polymer gel 12 has therein, that a light scattering material in use has a high interaction thereof with the stimulus-high polymer gel 12, electrically, in an ionic state and in other physical aspects, or that a light scattering material in use has a chemically modified surface. As light scattering materials whose surfaces are chemically modified, there can be exemplified: a light scattering material on whose surface there is provided a group chemically bonding with a stimulus-responsive high polymer gel 12 and a light scattering material to which a stimulus-responsive high polymer gel is grafted.

A concentration of a light modulation material (a light scattering material) included in a stimulus-responsive high polymer gel 12 is preferably at the lowest a value equal to or higher than a saturated scattering concentration when in shrinking of the stimulus-responsive high polymer gel 12.

Herein, a concentration equal to or higher than a saturated scattering concentration is a concentration as an index at which the average distance between light scattering material particles is sufficiently reduced and a light scattering action of the light scattering material particles alters from that of a primary particle to that of an agglomerated particle, with the result that a light scattering efficiency is altered. Such a state where a light scattering material shows a light scattering property characteristic of agglomerated light scattering particles is called a state where a concentration of a light scattering material is equal to or higher than a saturated scattering concentration. Further, another way of definition of a light scattering material concentration equal to or higher than a saturated scattering concentration goes this way: a light scattering material concentration at which a relationship between a light scattering material concentration and a scattered light amount under a condition of a specific optical path is largely deviated from a linear relationship.

In order to achieve a state where a concentration of a light scattering material is equal to or higher than a saturated scattering concentration, generally the concentration of a light scattering material included in a stimulus-responsive high polymer gel is preferably in the range of from 2 to 95% by wt and more preferably from 5 to 95% by wt of a total amount of a stimulus-responsive high polymer gel in a dry state although dependent on a particle diameter, a refractive index, a conductivity, a specific weight and others. If the light scattering material concentration is less than 2% by wt, the concentration is not equal to or higher than the saturated scattering concentration and thereby no change arises in scattered light amount to be caused by a change in volume of a stimulus-responsive high polymer gel 12, resulting in a problem such as that thicknesses of many light modulation layers are, in a case, required to be thicker in order to obtain a sufficient light modulation contrast. On the other hand, if the light scattering material concentration exceeds 95% by wt, no swelling/shrinking of a stimulus-responsive high polymer gel 12 occurs with good responsibility, thereby leading to a case where a stimulus responsive characteristic and a change in volume of a sensor material are reduced if a chance arises.

Moreover, a light scattering material may be included in a stimulus-responsive high polymer gel 12 in such a way that although a light scattering material concentration is equal to or lower than a saturated scattering concentration as a whole of the stimulus-responsive high polymer gel 12, a light scattering material concentration equal to or higher than the saturated scattering concentration can be realized locally in an agglomerated portion when the stimulus-responsive high polymer gel 12 is shrunk and the light scattering material particles are locally collected into the agglomerated portion.

In order to contain a light scattering material into a stimulus-responsive high polymer gel 12, the following methods are applied: a method in which a light scattering material is uniformly dispersed and mixed in a stimulus-responsive high polymer gel 12 prior to cross-linking and thereafter, cross-linking is performed in the high polymer gel 12; a method in which a light scattering material is added to a high polymer precursor composition prior to polymerization, followed by the polymerization; and other methods. In a case where a light scattering material is added prior to the polymerization, it is also preferable that a light scattering material having a polymerizable group or an unpaired electron (radical) is used as described above such that chemical bonding occurs in the polymerization. Moreover, it is preferable that a light scattering material is dispersed in as uniform a manner as possible in a high polymer gel. Especially when being dispersed into a high polymer, it is preferable that a light scattering material is uniformly dispersed by use of a mechanical kneading method, an agitation method, a dispersant or the like.

No specific limitation is imposed on a shape of a stimulus-responsive high polymer gel 12 and shapes thereof in use can be of various kinds such as particles, blocks, films and fibers, including a gel of no specific shape. Among them, a particulate state is especially preferable because of features of a high speed (responsibility) of a change in volume responding to various kinds of stimulus, a wide application range and others. No further limitation is imposed on particular shapes of a particle; applicable shapes are ones of various kinds, such as a sphere, a cube, an ellipsoid, a polyhedron, a porous particle, a star-like particle, a needle-like particle, a hollow particle and a scaly particle. In a case of a particle, a volume average diameter thereof in a shrunk state is preferably in the range of from 0.1 to 5 mm and more preferably from 1 $\mu$m to 1 mm. If the volume average diameter is less than 0.1 $\mu$m, problems have chances to arise such as that handling of particles becomes hard, and that no excellent optical property can be obtained. On the other hand, if the volume average diameter exceeds 5 mm, problems again have chances to arise such as that a response time required for a change in volume is delayed by a great margin.

Furthermore, the above-described particles can be produced by means of various methods, which are: a method in which a stimulus-responsive high polymer gel 12 is pulverized by means of a physical pulverizing method, a method in which a stimulus-responsive high polymer gel 12 prior to cross-linking is pulverized by means of a chemical pulverizing method and thereafter, cross-linking is performed to produce a stimulus-responsive high polymer gel 12 for use, and generally adopted methods, that is, methods for granular polymerization such as emulsion polymerization, suspension polymerization and dispersion polymerization.

Moreover, in order to attain a faster speed of a change in volume caused by various kinds of stimulus of a stimulus-responsive high polymer gel 12, it is also preferable that the stimulus-responsive high polymer gel 12 is prepared so as to be more porous by means of well known methods to thereby improve easiness in flowing out of liquid from or into the high polymer gel 12. In general, a stimulus-responsive high polymer gel 12 can be made porous by means of freeze-drying of the high polymer gel 12 in a swollen state.

A stimulus-responsive high polymer gel 12 can change a volume thereof by giving the high polymer gel 12 a stimulus as described above in the presence of a liquid that the stimulus-responsive high polymer gel 12 can absorb thereinto. For example, in a case of a thermal stimulus-responsive high polymer gel, a liquid can be absorbed in or released out to change a volume thereof by giving the high polymer gel radiation heat such as light or heat, in a case of an electrical stimulus-responsive high polymer gel, a liquid can be absorbed in or released out to change a volume thereof by a change in pH caused by an electrode reaction, ion adsorption caused by an electric field or an electrostatic action and in a case of an optical stimulus-responsive high polymer gel, a liquid can be absorbed in or released out to change a volume thereof by a change in internal structure caused by an influence of irradiation with light.

It is preferable judging from the above-described characteristics that in a sensor material of the present invention, a stimulus-responsive high polymer gel 12 is arranged in the presence of a liquid so as to absorb in or release out the liquid. That is, a sensor material of the present invention preferably has at least a liquid that is absorbed into or released out of a stimulus-responsive high polymer 12.

As a usable liquid in this case, a liquid is preferable that a stimulus-responsive high polymer gel 12 can absorb into or release out of itself. Furthermore, in a case where a high polymer constituting a stimulus-responsive high polymer gel 12 is not cross-linked, a liquid that can dissolve the high polymer therein can also be preferably adopted.

To be concrete, as liquids, there can be used: water, an aqueous solution of an electrolyte such as sodium chloride, potassium chloride, sodium hydroxide and potassium hydroxide; alcohols; ketones; esters; ethers; dimethylformamide, dimethylacetamide, dimethylsulfoxide, acetonitrile, propylene carbonate and others; and aromatic compound solvents such as xylene, toluene and others; and mixtures thereof.

Moreover, the liquids can be used with various kinds of additives, such as surfactants adsorbing to a stimulus-responsive high polymer gel 12, oxidation reduction agents including a biologen derivative to accelerate a change in pH of a liquid; dispersion stabilizers such as acid, alkali, salt and surfactant; stabilizers such as antioxidant and ultraviolet absorbing agent; and others. Furthermore, in order to color a liquid, colorants can be added to a liquid, such as various kinds of dyes and pigments. Colorants are preferable that imposes no adverse influence on swelling or shrinking of a stimulus-responsive high polymer gel. As concrete examples of the dyes, there can be named various dyes such as an azo dye, an anthraquinone dye, an indigo dye, a phthalocyanine dye, a carbonium dye, a quinonimine dye, a methin dye, a quinoline dye, a nitro dye, a benzoquinone dye, a naphthoquinone dye, a naphthalimide dye, a perinone and others and as concrete examples of the pigments, there can be named: carbon black, anthraquinone based pigment, azo based pigment, phthalocyanine based pigment, quinacridone based pigment, perylene based pigment, indigo based pigment and others.

A sensor material of the present invention can be used for detection of a living mater material with a simple contraction. As a detection method for a bio-substance, there can be named: for example, a detection method for a bio-substance using a sensor material of the present invention and detecting a change in tone based on swelling or shrinking of a stimulus-responsive high polymer gel.

Figure 2A:
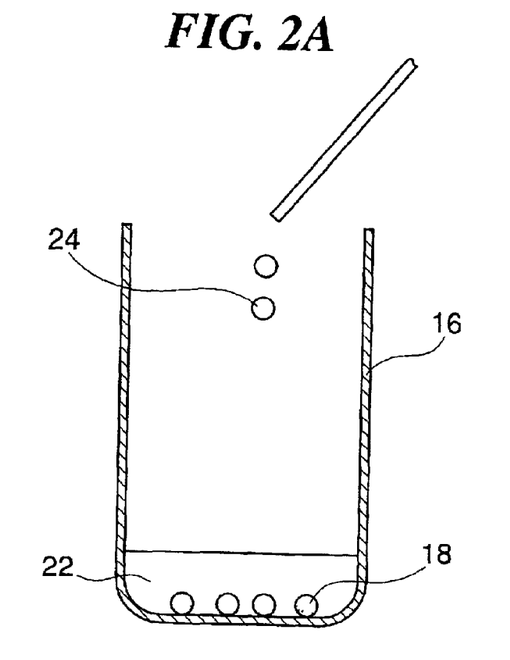
Figure 2B:
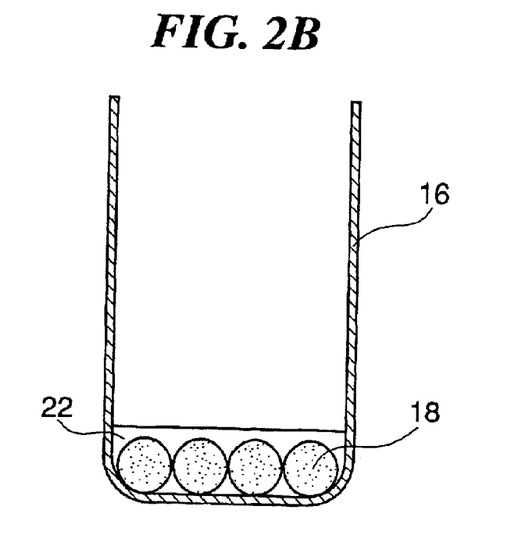

In FIGS. 2A and 2B, there are shown descriptive representations describing an example of a detection method for a bio-substance using a sensor material of the present invention. A sensor material 18 of the present invention (a stimulus-responsive high polymer gel containing at least both of a bio-substance-responsive material and a light modulation material) and a liquid 22 that the stimulus-responsive high polymer gel can absorb or release are put in a vessel 16 having an opening and when a liquid including a bio-substance (a bio-substance containing liquid 24) is added into the vessel 16 drop by drop, the bio-substance-responsive material inside the sensor material 18 reacts with a bio-substance to change pH inside the sensor material. The stimulus-responsive high polymer gel responds to the change in the pH to generate a change in volume (swelling) of the sensor material 18 as shown in FIG. 2B.

With the change in the volume, a change arises in absorbed light amount or scattered light amount of the sensor material to change a tone. A change in tone of the sensor material particles can be detected, for example, visually, when observed, to detect a bio-substance.

As the vessel 16, there can be named: a Petri dish, a dish, a test tube, a microtube, a microplate and others.

Note that even when a bio-substance-responsive material is not contained in a stimulus-responsive high polymer gel but is present outside the high polymer gel, a change in volume of the stimulus-responsive high polymer gel can be caused, by a similar principle, to detect a bio-substance.

Furthermore, in a sensor with such a configuration, a bio-substance-responsive material in a stimulus-responsive high polymer gel may flow out from the interior of the stimulus-responsive high polymer gel into a liquid therearound. In this case, the stimulus-responsive high polymer gel performs a change in volume by a change in pH caused by a reaction between the bio-substance-responsive material in the liquid inside and outside the stimulus-responsive high polymer gel and the bio-substance. With this change in the volume, an optical change arises in a sensor material of the present invention to enable the bio-substance to be detected.

Note that a sensor material is put on a microplate with many of wells as the vessel 16 in advance and when a bio-substance containing liquid 24 is added drop by drop into plural wells, a number of specimens can be simultaneously measured.

Furthermore, transmitting light is directed to a sensor using a sensor material of the present invention described later and a bio-substance can be detected by means of a transmitting light detection method detecting transmitting light based on swelling and shrinking of the sensor material (the stimulus-responsive high polymer gel).

Sensor

A sensor of the present invention is constituted of at least an already described sensor material and an optical waveguide.

A configuration of a sensor has only to be such that a bio-substance and a sensor material are reacted with each other and a change in tone of the sensor material can be detected using transmitting light or the like.

For example, various inventive constructions can be conceived including, as an example, one in which a sensor material of the present invention is put in a vessel in a syringe-like shape, a liquid including a bio-substance to be detected is extracted from a living body or the like and by reacting the bio-substance with the sensor material, a detection of the bio-substance is performed.

Figure 3A:
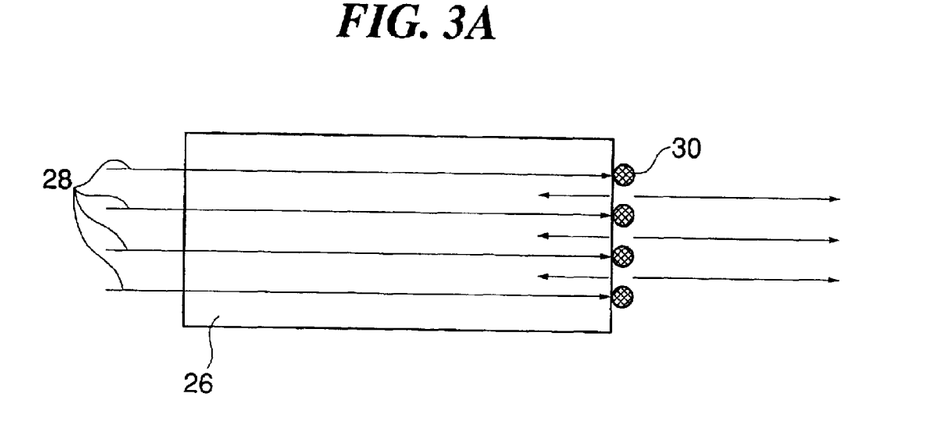
Figure 3B:
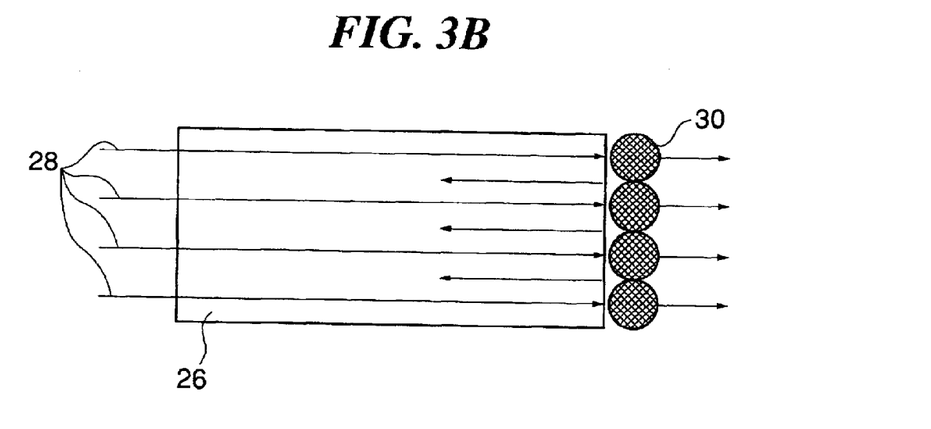

In FIGS. 3A and 3B, there is shown a configuration of a sensor of the present invention.

A sensor shown in FIGS. 3A and 3B is constructed of an optical waveguide 26 and a sensor material 30 provided to an optical waveguiding section at an end of the optical waveguide 26. FIG. 3A shows a shrunk state of the sensor material 30 while FIG. 3B shows a swollen state of the sensor material 30 that has reacted with a bio-substance. To the contrary, according to a combination of a bio-substance-responsive material and the bio-substance, a case arise where the sensor material 30 goes into a contacted state as shown in FIG. 3A by a reaction between the sensor material 30 in a swollen state as shown in FIG. 3B and the bio-substance.

In a shrunk state of the sensor material 30 as shown in FIG. 3A, if light 28 is applied from the side of the optical waveguide 26 to which the sensor material 30 is not provided, almost all of the light 28 is detected as transmitting light.

On the other hand, in a swollen state of the sensor material 30 as shown in FIG. 3B, if light 28 is applied from the side of the optical waveguide 26 to which the sensor material 30 is not provided, almost all of the light 28 applied is transmitted through the swollen sensor material 30 to change a tone or the like thereof. By detecting of such transmitting light, qualitative and quantitative analyses of a bio-substance are enabled.

As an optical waveguide 26 of a sensor, a general purpose optical waveguide can be adopted, which are, for example, an optical fiber such as a plastic optical fiber (POF) and a quartz optical fiber; a thin film waveguide such as a slab waveguide constructed of a planar dielectric thin film, a two-dimensional waveguide such as a planar waveguide; a patterned waveguide obtained by patterning a two-dimensional waveguide; and a three-dimensional waveguide such as a channel waveguide; and others.

A sensor material 30 is preferably provided to an optical waveguiding section of the optical waveguide 26 at least in a close contact or an adjacent state thereto. When the sensor material 30 is provided in such a state, much of light can be directed to the sensor material 30 and at the same time, more of reflecting light on and more of transmitted through the sensor material 30 can be passed through the optical waveguide 26. Such a configuration can be realized by a method where a sensor material, as shown in FIGS. 3A and 3B, is fixed directly to the optical waveguiding section or the like method, when the sensor material is put into close contact with the optical waveguiding section.

In order to fix the sensor material 30 directly to the optical waveguide 26 as shown in FIGS. 3A and 3B, there is adopted a method for adhering the sensor material 30 to the optical waveguide 26 or the like method using a physical fixing treatment using an adhesive, a chemical fixing treatment using various fixing agents or the like.

As an adhesive used in a physical fixing treatment, there can be named, for example: general purpose adhesives such as an organic solvent evaporation adhesive, a thermosetting reaction adhesive, a moisture curing reaction adhesive, an ultraviolet curing reaction adhesive, a condensation reaction adhesive, an addition reaction adhesive, a heat fusion adhesive and others, and an adhesive in use is preferably achromatic at least in a visible region when fixing.

As various fixing agents used in a chemical fixing treatment, there can be named: compounds having two or more polymerizable unsaturated groups and other groups, such as ethylene glycol di(meth)acrylate, propylene glycol di(meth)acrylate, polyethylene glycol di(meth)acrylate, polypropylene glycol di(meth)acrylate, N,N'-methylene bis (meth)acrylamide; and compounds having two or more reactive functional groups and other groups, such as ethylene glycol diglycidyl ether, hexamethylen di-isocyanate, silane coupling agents including 3,4-epoxybutyl trimethoxysilane, [3-glycidoxypropyl] bis [trimethylsiloxy] methylsilane, [3-glycidoxypropyl] dimethylethoxysilane, [3-glycidoxypropyl] methyldiethoxysilane, [3-glycidoxypropyl] pentamethyl disiloxane, [3-glycidoxypropyl] trimethoxysilane, 3-isocyanato propyltriethoxysilane; and others.

Note that the term (meth)acrylic in the concrete examples means both of (meth)acrylic and acrylic.

As concrete processes for the physical fixing treatment, there can be named: a process in which an adhesive solution is prepared by dissolving an adhesive into a solvent, the prepared solution is applied on an optical waveguide 26, thereafter, a sensor material 30 is sprayed and heat treatment is given to fix the sensor material; a process in which a mixture of a sensor material 30 and particulate adhesive is attached to an optical waveguide 26 and thereafter, heat treatment is applied to fix the sensor material 30; and other methods.

As concrete methods for the chemical fixing treatment, there can be adopted a method in which a sensor material 30 and one of various fixing agents are applied to an optical waveguide 26 by means of a method for coating, spraying or impregnation and the sensor material 30 and the fixing agent are heated to an inherent reaction temperature thereof to form a chemical bond and fix the sensor material 30 to the optical waveguide 26. A sensor thus fabricated has the sensor material 30 exposed to the outside, so detection of a bio-substance can be achieved by putting the sensor material 30 into contact with an external liquid.

Figure 4A:
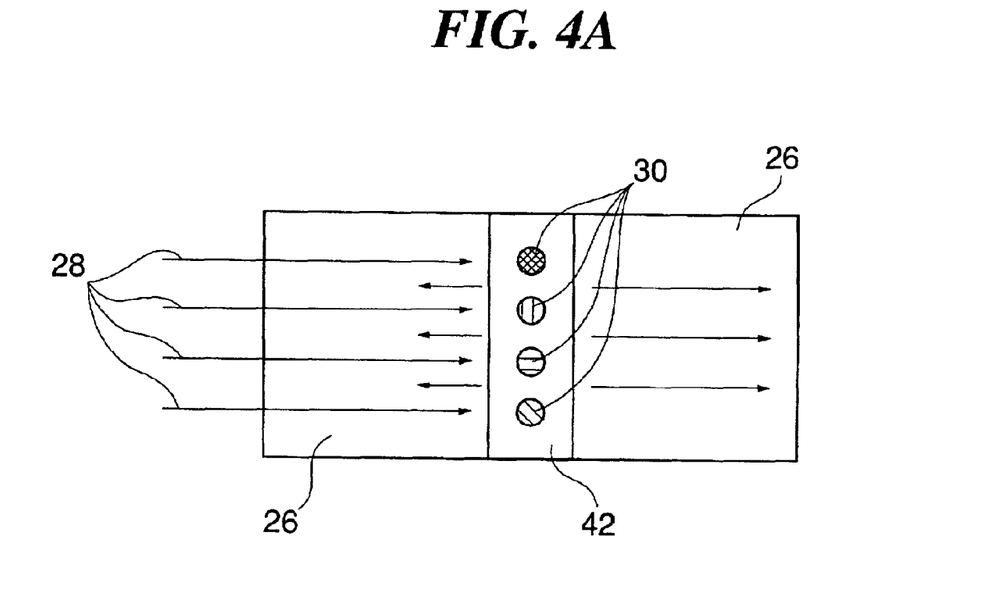
Figure 4B:
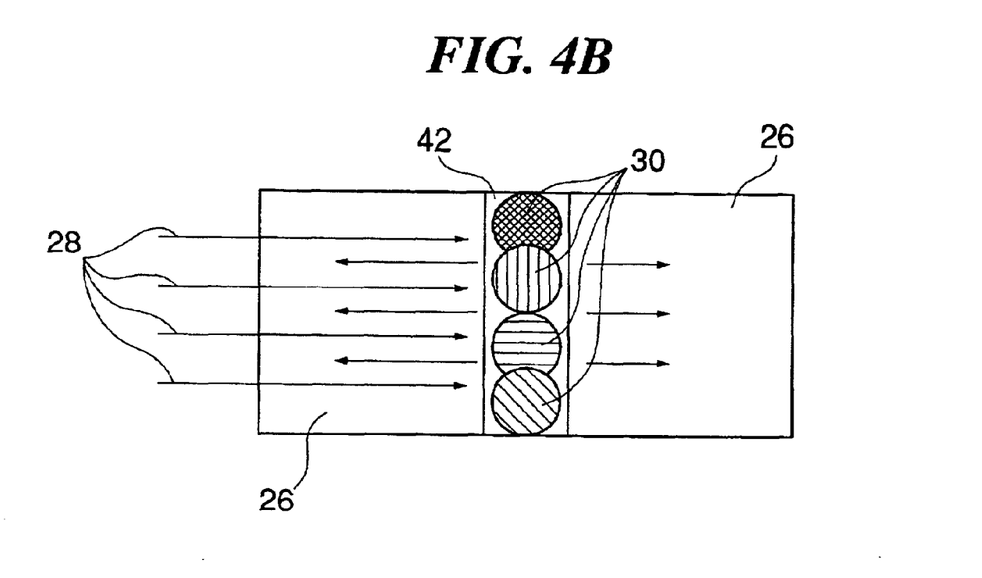

Furthermore, when a sensor material 30 is placed close to an optical waveguide 26, the close placement can be realized by fixing a sensor member 42 in a sheet including the sensor material 30 to the optical waveguide 26 as shown in FIGS. 4A and 4B.

Note that the embodiment shown in FIGS. 4A and 4B is only an example and if other methods for placing a sensor material 30 are available in addition to the embodiment, one of the other methods can be properly implemented.

A sensor shown in FIGS. 4A and 4B is constructed of an optical waveguide 26 and a sheet-like sensor member 42 including a sensor material 30 provided to an optical waveguiding section somewhere in the optical waveguide 26. FIG. 4A shows a shrunk state of the sensor material 30 while FIG. 4B shows a state of the sensor material swollen by a reaction between the sensor material 30 and a bio-substance. To the contrary, a case occurs, according to a combination of a bio-substance-responsive material and the bio-substance, where the sensor material 30 in a swollen state as shown in FIG. 4B reacts with the bio-substance to shrinks as shown in FIG. 4A.

When light 28 is applied from the optical waveguiding section in a shrunk state of a sensor material 30 as shown in FIG. 4A, almost all of light 28 applied is transmitted through to be detected.

On the other hand, when light 28 is applied from the side of the sensor material to which the sensor material 30 is not provided as shown in FIG. 4B in a swollen state of the sensor material 30, almost all of the light 28 applied is transmitted through the swollen sensor material 30 to change a tone or the like thereof. By detecting of such transmitting light, qualitative and quantitative analyses of a bio-substance are enabled. Herein, if the sensor material 30 alters differently in color according to a bio-substance to be detected, qualitative and quantitative analyses of plural kinds of bio-substances can be simultaneously performed.

That is, when a sensor material 30 with which if glucose reacts, a blue color is decolored is adhered to an optical waveguiding section and a sensor material 30 with which if sucrose reacts with, a yellow color is decolored is adhered to another optical waveguiding section, a sensor capable of simultaneously detecting glucose and sucrose can be fabricated.

As sensor members 42 shown in FIGS. 4A and 4B, there can be named, to be concrete: a sensor member containing a sensor material 30 in a cell; a sensor member having a sensor material 30 included in a porous material; a sensor member in which a sensor material 30 is fixed to a fibrous base; and others. A preferable sensor of the present invention can be fabricated by adhering each of the sensor members 42 to an optical waveguiding section in close contact therewith using an adhesive or the like. Furthermore, a sensor member 42 may be adhered to plural optical waveguiding sections as shown in FIGS. 4A and 4B in close contact therewith. In a case where such a construction is adopted, a kind and an amount of external stimulus in a measuring atmosphere and others can be measured from transmitting light or the like of a sensor member 42.

Note that in a case of a sensor member containing a sensor material 30 in a cell, there can be adopted a sensor material having a bio-substance-responsive material being outside a stimulus-responsive high polymer gel.

As adhesives used in fixing a sensor member 42, there can be named, for example: general purpose adhesives such as an organic solvent evaporation adhesive, a thermosetting reaction adhesive, a moisture curing reaction adhesive, an ultraviolet curing reaction adhesive, a condensation reaction adhesive, an addition reaction adhesive, heat fusion adhesive and others, and an adhesive in use is preferably achromatic at least in a visible region when fixing. As a concrete process for a fixing treatment using one of the adhesives, a general process can be adopted such as one in which an adhesive solution is prepared by dissolving an adhesive into a solvent, the prepared solution is applied to an optical waveguiding section, then the optical waveguiding section is mounted to a sensor member and finally the section and the member receive heat treatment for fixing.

As a sensor member 42 including a sensor material 30 in a cell, there can be exemplified, to be concrete: a cell in which a sensor material 30 is held between a pair of bases with spacers interposing therebetween.

As bases, there can be used: high polymer films or sheet bases of polyester, polyimide, poly(methyl(meth)acrylate, polystrene, polypropylene, polyethylene, Nylon, polyvinyl chloride, polyvinylidene chloride, polysulfone, polycarbonate, polyether, cellulose derivative and others; or a glass base; a metal base; a ceramic base; and others. However, a sensor member is indispensably of a structure that light from an optical waveguiding section is directed to a sensor material 30 therein; therefore, at least one of the two bases has to be selected as an optically transparent material. A spacer in use can be publicly known.

Furthermore, a sensor shown in FIGS. 4A and 4B requires a bio-substance-responsive material in a sensor material 30 to be put into contact with a material to be detected (a bio-substance). For this reason, a cell has to be an open type so as to be able to contact an external liquid. Therefore, for example, a necessity arises for use of a porous base as a base or a cell with an opening.

Furthermore, in a case of a sensor member in which a sensor material 30 is included in a porous material, at least a porous material transparent and with less of light scattering can be adopted as the porous material. A general purpose porous glass material, a porous high polymer and others can be adopted, for example. While a sensor member can be fabricated by making a sensor material contained into a porous material, various processes for the containment can be adopted, for example: such as a process in which when a bio-substance-responsive material, a colorant and a light scattering material are uniformly dispersed and mixed into a stimulus-responsive high polymer gel, a porous material is impregnated with this dispersion/mixture and thereafter, the dispersion/mixture is cross-linked; and a process in which when a bio-substance-responsive material, a colorant and a light scattering material are uniformly dispersed and blended into a stimulus-responsive high polymer precursor composition, a porous material is impregnated with this dispersion/mixture and thereafter the dispersion/mixture is polymerized. Since the sensor member is formed with a porous material, the member is of an open type capable of contacting an external liquid. Moreover, a distal end of a sensor is mounted with a light waveguiding section and a strength of the distal end is stronger than in a case where the sensor material is exposed. Therefore, a sensor member in this shape and condition is suited for applications such as detection of a bio-substance penetrating into the interior of a bio-material and the like.

In addition, in a case of a sensor member in which a sensor material is fixed to a fibrous base, there can be adopted as fiber bases: such as of synthetic fibers including Nylon fiber, acrylic fiber, polyester fiber, polypropylene fiber, polyvinyl chloride fiber, polyamide fiber, polyurethane fiber and others; natural fibers including wood pulp, cotton, sheep wool and others; semi-synthetic fibers including viscose rayon, acetate, cupra and others; and inorganic fibers including carbon fiber, titanium fiber and others.

Among them, synthetic fibers and semi-synthetic fibers are especially preferable. As shapes and conditions of a fibrous base, there can be named: in addition to a simple assembly of fibers, a structure such as fabric, unwoven cloth, web and sheet. A sensor member can be fabricated by fixing a sensor material to a fibrous base and as a fixing method, there can be adopted: mechanical fixing, physical fixing by an adhesive, chemical fixing by chemical bonds or the like. Note that as the chemical bond, there can be conceived various kinds of bonds such as ionic bond, hydrogen bond, covalent bond and others, and among them, a covalent bond is preferable in terms of stability.

Mechanical fixing is to hold a sensor material mainly in interstices or the like between fibers of a base. As the mechanical fixing, there can be adopted: a method in which a sensor material is sprayed on a fibrous base to fill spaces such as interstices between fibers and other methods. As an adhesive used in the physical fixing, there can be adopted: adhesives used in direct fixing of a sensor material to an optical waveguiding section. The physical fixing is performed by means of various processes such as a process in which an adhesive solution is prepared by dissolving an adhesive into a solvent, the prepared solution is applied on a fibrous base and thereafter, a sensor material is sprayed and the resultant base is subjected to heat treatment to fix the sensor material on the base; and a process in which a mixture of a sensor material and a particulate adhesive is sprayed on a fibrous base and thereafter, the sprayed fibrous base is subjected to heat treatment to fix the sensor material on the base.

Furthermore, as chemical fixing by a chemical bonding and others, there can be preferably adopted: fixing by reactions of various kinds of fixing agents. As the various fixing agents, there can be adopted: various fixing agents used in direct fixing of a sensor material to an optical waveguiding section. As chemical fixing using the various fixing agents, there can be adopted a process in which a sensor material and various fixing agents are applied on a fibrous base by means of a method such as coating, spraying, impregnation or others and the coated fibrous base, for example, is subjected to heat treatment at a reaction temperature inherent in the various fixing agents to form chemical bonding for fixing or other processes. Since such a sensor material is formed from a fibrous base, an open type is adopted in which a bio-substance-responsive material in the sensor material can contact a material to be detected and the sensor member assumes a shape suitable for a sensor of the present invention.

A sensor fabricated in such a way can be used as a sensor for a blood sugar value in vivo, for example, by incorporating the sensor in a catheter or embedding the sensor directly under a skin. In a case where an artificial part is put into a living matter to be put into direct contact with a living matter component such as blood or proteins, compatibility of the artificial part with the living matter is an important factor.

However, a sensor material of the present invention is made up of hydrogel which is generally said to have a high compatibility with a living matter and furthermore, it is expected that by use of a high polymer material especially excellent in compatibility with a living matter among the hydrogels, a sensor material excellent in compatibility with a living matter can be obtained. By use of such a sensor material, there arises a possibility of realizing a sensor having a better sensitivity than a prior art sensor in which a transmittance changes by agglomerates produced between an antibody and a bio-substance in gel; whose configuration is simpler and more convenient than a prior art sensor measuring a bio-substance using apparatuses such as an ammeter and others; and excellent in compatibility with a living matter.

EXAMPLES

A description will be given of the present invention in a more concrete manner taking up examples, but the present invention is not limited to the description of the examples.

Example 1

Preparation of Sensor Material

Prepared as described below was a stimulus-responsive high polymer gel including glucose oxidase, catalase and a light modulation material.

Used as a light modulation material was phthalocyanine blue pigment (made by Dainichiseika Colour & Chemicals Mfg.) and used as an enzyme were glucose oxidase and catalase. Added into 20 ml of a distilled water were 2.6 g of phthalocyanine blue pigment and 0.8 g of sodium dodecyl sulfate and the additives were uniformly dispersed by an ultrasonic method into a mixed solution.

Added into the mixed solution were 3 g of sodium acrylate and 3 g of acrylamide as main monomers, and 1.2 g of glucose oxidase and 0.06 g of catalase as enzymes and 0.03 g of methylene bis-acrylamide as a cross-linking agent and the resultant mixture was dispersed using a planetary mill for 1 hour to prepare a reaction solution.

Nitrogen gas was blown into the resultant reaction solution for 5 minutes or more to sufficiently remove dissolved oxygen therein. Three liters of a toluene solution in which 9 g of stearyl alcohol was dissolved was added into a separable flask containing the reaction solution on which nitrogen substitution had been performed. Thereafter, the reaction solution was agitated at room temperature (which means and will means 25° C. hereinafter) for 10 minutes with rotary agitating blades rotating at 600 rpm while blowing nitrogen gas thereinto to attain a state of stable suspension. Thereafter, 5.94 g of 0.67 wt % ammonium persulfate aqueous solution was added to the reaction solution to further progress a reaction therein for 8 hours while agitating at 300 rpm, thereby preparing stimulus-responsive high polymer gel particles including a light modulation material, glucose oxidase and catalase.

Thus prepared stimulus-responsive high polymer gel particles were separated and washed with distilled water repeatedly. Thereafter, the particles were screened using a mesh to obtain the stimulus-responsive high polymer gel particles as a sensor material having the volume average particle diameter of 30 $\mu$m in a swollen state.

Evaluation of Characteristics of Sensor Material

Evaluation of the characteristics was performed on thus prepared sensor material (stimulus-responsive high polymer gel particles) as described below.

First of all, the prepared particulate sensor material was added into distilled water to obtain a sensor material dispersion liquid in which the material was dispersed at a concentration (0.12 g/liter) and the dispersion liquid was put on a V-bottom microplate. In order to investigate a relationship between an additive amount and a transmittance, a glucose containing phosphoric acid buffer liquid of pH 7.4, which was a bio-substance, was added to the microplate after deaeration, at which time a transmittance was measured. As a result, it was confirmed that when a glucose concentration in the added buffer solution was increased over 0 to 20 mM, a transmittance of the sensor material dispersion liquid significantly changed from 60% to 10%.

It has been known that glucose oxidase and catalase included in a sensor material decompose glucose to reduce pH. On the other hand, a stimulus-response high polymer gel constituting the sensor material has a nature that the high polymer gel shrinks with decrease in pH and a light absorption efficiency and others of the stimulus-responsive high polymer gel decreases in company with the shrinking.

Therefore, an observed change in transmittance is considered as a result of a phenomena that by addition of glucose, pH inside the sensor material decreases and thereby the stimulus-responsive high polymer gel shrinks to reduce a light absorption efficiency and others thereof, so a transmittance of the sensor material dispersion liquid increases.

Accordingly, the sensor material of Example 1 was found to be a high sensitivity sensor material that a transmittance significantly changed in a low glucose concentration region by swelling or shrinking of the stimulus-responsive high polymer gel constituting the sensor material.

Fabrication of Sensor and Evaluation of Characteristics

A sensor was fabricated using the prepared sensor material.

To be detailed, there were adopted two optical fibers 1 mm in diameter as optical waveguide and a cell including the sensor material. A sensor as detailed below was fabricated in which distal ends of the optical fibers were fixed at both side surfaces of the cell such that light emitted from an optical fiber passed through the cell and was further directed to another optical fiber.

First of all, a composition was prepared in which the sensor material included in the cell is dispersed in a phosphoric acid buffer liquid of pH 7.4 to be swollen. Then, a cellophane tube of 1 mm in diameter as a cell was prepared and one end of the cell was mounted to the distal end of an optical fiber. The sensor material was injected into the cellophane tube, modulation was performed such that a distance between the two optical fibers is 100 $\mu$m and an optical fiber was fixed to the other end of the cell, whereby a sensor was fabricated in which the optical fibers were in close contact with the cell.

Evaluation of characteristics as described below was performed on thus fabricated sensor.

A phosphoric acid buffer liquid of pH 7.4 including 0 to 20 mM of glucose was prepared and after deaeration, the cell section of the sensor was immersed in the buffer liquid to measure a transmittance. As a result, a large change in transmittance from 10 to 70% was obtained according to a glucose concentration. This operation was repeated plural times and similar transmittances were obtained.

It was found from the above-described results of evaluation that a glucose concentration in a measuring atmosphere of a sensor could be sensed by measuring a light transmittance for light directed to an optical fiber of a sensor of the present invention, whose construction is simple. Furthermore, it was found that the sensor was of a high sensitivity because an optical density significantly changed in a low glucose concentration region as well.

Example 2

Preparation of Sensor Material

Used as a light modulation material was 2.6 g of phthalocyanine blue pigment (made by Dainichiseika Colour & Chemicals Mfg.) and the material was added into 20 ml of distilled water including 0.8 g of sodium dodecyl sulfate and the additives were uniformly dispersed by an ultrasonic method into a mixed solution. Added into the mixed solution were 3 g of sodium acrylate and 3 g of acrylamide as main monomers, and 0.03 g of a methylene bis-acrylamide as a cross-linking agent and the resultant mixture was dispersed using a planetary mill for 1 hour to prepare a reaction solution.

Nitrogen gas was blown into the resultant reaction solution for 5 minutes or more to sufficiently remove dissolved oxygen therein. Three liters of a toluene solution in which 9 g of stearyl alcohol was dissolved was added into a separable flask containing the reaction solution on which nitrogen substitution had been performed. Thereafter, the reaction solution was agitated at room temperature for 10 minutes with rotary agitating blades rotating at 600 rpm while blowing nitrogen gas thereinto to attain a state of stable suspension. Thereafter, 5.94 g of 0.67 wt % ammonium persulfate aqueous solution was added to the reaction solution to further progress a reaction therein for 8 hours while agitating at 300 rpm, and thereby there was prepared stimulus-responsive high polymer gel particles including a light modulation material.

Thus prepared stimulus-responsive high polymer gel particles were separated and washed with distilled water repeatedly. Thereafter, the particles were screened using a mesh to obtain the stimulus-responsive high polymer gel particles as a sensor material having the volume average particle diameter of 30 $\mu$m in a swollen state.

Evaluation of Characteristics of Sensor Material

Evaluation of the characteristics was performed on thus prepared sensor material (stimulus-responsive high polymer gel particles) as described below.

First of all, the prepared particulate sensor material was added into distilled water to obtain a sensor material dispersion liquid in which the material was dispersed at a concentration (0.12 g/liter) and the dispersion liquid was put on a V-bottom microplate. Thereafter, 0.015 g of glucose oxidase and 0.001 g of catalase, as enzymes, were added to the dispersion liquid on the V-bottom microplate. A relationship between an additive amount and a transmittance was investigated in a similar manner to Example 1 and as a result, it was confirmed that a transmittance of the sensor material dispersion liquid significantly changed from 60% to 10%.

It has been known that glucose oxidase and catalase included in a sensor material decompose glucose to reduce pH. On the other hand, a stimulus-response high polymer gel constituting the sensor material has a nature that the high polymer gel shrinks with decrease in pH and a light absorption efficiency and others of the stimulus-response high polymer gel decreases in company with the shrinking.

Therefore, an observed change in transmittance is considered as a result of a phenomena that by addition of glucose, pH inside the sensor material decreases and thereby the stimulus-responsive high polymer gel shrinks to reduce a light absorption efficiency and others thereof, so a transmittance of the sensor material dispersion liquid increases.

Accordingly, the sensor material of Example 2 was found to be a high sensitivity sensor material that a transmittance significantly changed in a low glucose concentration region by swelling or shrinking of the stimulus-responsive high polymer gel constituting the sensor material.

Example 3

Preparation of Sensor Material

Prepared as described below was a stimulus-responsive high polymer gel including glucose oxidase, catalase and a light modulation material.

Used as a light modulation material was phthalocyanine blue pigment (made by Dainichiseika Colour & Chemicals Mfg.) and used as an enzyme were glucose oxidase and catalase. Added into 20 ml of a distilled water were 2.6 g of phthalocyanine blue pigment and 0.8 g of sodium dodecyl sulfate and the additives were uniformly dispersed by an ultrasonic method into a mixed solution. Added into the mixed solution were 2 g of sodium acrylate and 0.8 g of dimethylaminopropyl methacrylamide as main monomers, and 1.2 g of glucose oxidase and 0.06 g of catalase as enzymes and 0.03 g of methylene bis-acrylamide as a cross-linking agent, and the resultant mixture was dispersed using a planetary mill for 1 hour to prepare a reaction solution.

Thus obtained reaction solution was treated in a similar manner to Example 1 and thereby there was prepared stimulus-responsive high polymer gel particles including a light modulation material, glucose oxidase and catalase.

Thus prepared stimulus-responsive high polymer gel particles were separated and washed with distilled water repeatedly. Thereafter, the particles were screened using a mesh to obtain the stimulus-responsive high polymer gel particles as a sensor material having the volume average particle diameter of 30 $\mu$m in a swollen state.

Evaluation of Characteristics of Sensor Material

Evaluation of the characteristics was performed on thus prepared sensor material (stimulus-responsive high polymer gel particles) according to a similar method to Example 1. Investigation was performed on a relationship between an additive amount and a transmittance and it was confirmed that when a glucose concentration in the added buffer solution was increased over 0 to 20 mM, a transmittance of the sensor material dispersion liquid significantly changed from 5% to 90%.

Therefore, similarly to Example 1, an observed change in transmittance is considered as a result of a phenomena that by addition of glucose, pH inside the sensor material decreases and thereby the stimulus-responsive high polymer gel shrinks to reduce a light absorption efficiency and others thereof, so a transmittance of the sensor material dispersion liquid significantly increases.

Accordingly, the sensor material of Example 3 was found to be a high sensitivity sensor material that a transmittance significantly changed in a low glucose concentration region by swelling or shrinking of the stimulus-responsive high polymer gel constituting the sensor material.

Fabrication of Sensor and Evaluation of Characteristics

A sensor of the present invention was fabricated using the prepared sensor material in a similar manner to Example 1 and evaluation of characteristics of the sensor was performed in a similar method to Example 1. As a result, a large change in transmittance from 5 to 90% was obtained according to a glucose concentration. This operation was repeated plural times and similar transmittances were obtained.

It was found from the above-described results of evaluation that a glucose concentration in a measurement atmosphere of a sensor was be able to be sensed in a similar manner to Example 1 and that the sensor of Example 3 was of a high sensitivity because an optical density significantly changed in a low glucose concentration region as well.

Example 4

Preparation of Sensor Material

Used as a light modulation material was 2.6 g of phthalocyanine blue pigment (made by Dainichiseika Colour & Chemicals Mfg.) and the material was added into 20 ml of distilled water including 0.8 g of sodium dodecyl sulfate and the additives were uniformly dispersed by an ultrasonic method into a mixed solution. Added into the mixed solution were 2 g of sodium acrylate and 0.8 g of dimethylaminopropyl methacrylamide as main monomers, and 0.03 g of a methylene bis-acrylamide as a cross-linking agent and the resultant mixture was dispersed using a planetary mill for 1 hour to prepare a reaction solution.

Thus obtained reaction solution was treated in a similar manner to Example 2 and thereby there was prepared stimulus-responsive high polymer gel particles including a light modulation material.

Thus prepared stimulus-responsive high polymer gel particles were separated and washed with distilled water repeatedly. Thereafter, the particles were screened using a mesh to obtain the stimulus-responsive high polymer gel particles as a sensor material having the volume average particle diameter of 30 μm in a swollen state.

Evaluation of Characteristics of Sensor Material

Investigation was performed on a relationship between an added amount and a transmittance of thus prepared sensor material (stimulus-responsive high polymer gel particles) according to a similar manner to evaluation of characteristics in Example 2 and it was confirmed that a transmittance of the sensor material dispersion liquid significantly changed from 5% to 90%.

Therefore, similarly to Example 2, an observed change in transmittance is considered as a result of a phenomena that by addition of glucose, pH inside the sensor material decreases and thereby the stimulus-responsive high polymer gel shrinks to reduce a light absorption efficiency and others thereof, so a transmittance of the sensor material dispersion liquid significantly increases.

Accordingly, the sensor material of Example 4 was found to be a high sensitivity sensor material that a transmittance significantly changed in a low glucose concentration region by swelling or shrinking of the stimulus-responsive high polymer gel constituting the sensor material.

Example 5

Preparation of Sensor Material

Prepared as described below was a stimulus-responsive high polymer gel including urease and a light modulation material.

Used as a light modulation material was phthalocyanine blue capsule pigment (made by Dainippon Ink & Chemicals) at a pigment concentration of 13.5 wt % and urease as an enzyme was used. Added to 20 g of phthalocyanine blue capsule pigment as the light modulation material were 5.8 g of N-isopropyl acrylamide and 0.2 g of acrylic acid as main monomers, and 40 mg of urease as an enzyme and 0.03 g of methylene bis-acrylamide as a cross-linking agent and the resultant mixture was dispersed using a planetary mill for 1 hour to prepare a reaction solution.

Nitrogen gas was blown into the resultant reaction solution for 5 minutes or more to sufficiently remove dissolved oxygen therein. Three liters of a toluene solution in which 4.4 g of sorbitol surfactant (made by Dai-ichi Kogyo Seiyaku with a trade name of Solgen 50) was dissolved was added into a separable flask containing the reaction solution on which nitrogen substitution had been performed. Thereafter, the reaction solution was agitated at room temperature for 10 minutes with rotary agitating blades rotating at 600 rpm while blowing nitrogen gas thereinto to attain a state of stable suspension. Thereafter, 5.94 g of 0.67 wt % ammonium persulfate aqueous solution was added to the reaction solution and the separable flask was immersed into a water bath at 70° to further progress a reaction therein for 8 hours while agitating at 300 rpm, thereby preparing stimulus-responsive high polymer gel particles including urease.

Thus prepared stimulus-responsive high polymer gel particles were separated and washed with distilled water repeatedly. Thereafter, the particles were screened using a mesh to obtain the stimulus-responsive high polymer gel particles having the volume average particle diameter of 30 μm in a swollen state and urease.

Evaluation of Characteristics of Sensor Material

Evaluation of the characteristics as describe below was performed on thus prepared sensor material (stimulus-responsive high polymer gel particles), wherein a bio-substance was urea.

First of all, thus prepared particulate sensor material was added into an acidic substrate solution of pH 3 at a temperature of 33.5° to obtain a sensor material dispersion liquid in which the material was dispersed at a concentration (0.12 g/liter) and the sensor material dispersion liquid was put in place on a V-bottom microplate.

At this time, the stimulus-responsive high polymer gel was in a shrunk state under conditions of temperature of 33.5° C. and pH as low as 3 and therefore, a transmittance of the sensor material dispersion liquid was high.

In order to investigate a relationship of an additive amount of urea and a transmittance, an urea aqueous solution (pH 4), which was a bio-substance, after deaeration was added onto the microplate to measure a transmittance at the time while keeping a temperature at 33.5° C. As a result, it was confirmed that when a urea concentration in the added solution was increased over 0 to 20 mM, a transmittance of the sensor material dispersion liquid significantly changed from 70% to 10%.

It has been known that urease included in a sensor material hydrolyzes urea to raise pH. On the other hand, a stimulus-response high polymer gel constituting the sensor material has a nature that the high polymer gel swells with increase in pH to raise a light absorption efficiency and others thereof in company with the swelling. Therefore, an observed change in transmittance is considered as a result of a phenomena that by addition of urea, pH inside the sensor material rises and thereby a stimulus-response high polymer gel swells to increase a light absorption efficiency and others thereof and in turn reduce a transmittance of a sensor material dispersion liquid.

Accordingly, the sensor material of Example 5 was found to be a high sensitivity sensor material in which a transmittance significantly changed in a low glucose concentration region by swelling or shrinking of the stimulus-responsive high polymer gel constituting the sensor material.

Fabrication of Sensor and Evaluation of Characteristics

A sensor was fabricated using thus prepared sensor material in a similar manner to Example 1 and evaluation of characteristics of the sensor as described below was performed.

First of all, a urea aqueous solution of pH 4 including 0 to 20 mM of urea was prepared and after deaeration, the cell section of the sensor was immersed in the aqueous solution to measure a transmittance while keeping a measurement temperature at 33.5° C. As a result, a large change in transmittance from 80 to 5% was obtained according to a urea concentration. This operation was repeated plural times and similar transmittances were obtained.

It was found from the above-described results of evaluation that a glucose concentration in a measuring atmosphere of a sensor could be sensed by measuring a light transmittance of an optical fiber of a sensor of the present invention for light incident on the optical fiber. Furthermore, it was found that the sensor of Example 5 was of a high sensitivity because an optical density significantly changed in a low glucose concentration region as well.

Example 6

Preparation of Sensor Material

Prepared as described below was a stimulus-responsive high polymer gel including a glucose oxidant and Co(II) phthalocyanine pigment as a light modulation material.

Added to 20 ml of distilled water were 2.6 g of Co(II) phthalocyanine pigment as the glucose oxidant and the light modulation material and 0.8 g of sodium dodecyl sulfate and the additives were uniformly dispersed by an ultrasonic method into a mixed solution. Added to the mixed solution were 3 g of sodium acrylate and 3 g of acrylamide as main monomers and 0.03 g of methylene bis-acrylamide as a cross-linking agent and the resultant mixture was dispersed using a planetary mill for 1 hour to prepare a reaction solution.

Nitrogen gas was blown into the resultant reaction solution for 5 minutes or more to sufficiently remove dissolved oxygen therein. Three liters of a toluene solution in which 9 g of stearyl alcohol was dissolved was added into a separable flask containing the reaction solution on which nitrogen substitution had been performed. Thereafter, the reaction solution was agitated at room temperature for 10 minutes with rotary agitating blades rotating at 600 rpm while blowing nitrogen gas thereinto to attain a state of stable suspension. Thereafter, 5.94 g of 0.67 wt % ammonium persulfate aqueous solution was added to the reaction solution to further progress a reaction therein for 8 hours while agitating at 300 rpm, thereby preparing stimulus-responsive high polymer gel particles including a glucose oxidant and a light modulation material.

Thus prepared stimulus-responsive high polymer gel particles were separated and washed with distilled water repeatedly. Thereafter, the particles were screened using a mesh to obtain the stimulus-responsive high polymer gel particles having the volume average particle diameter of 30 μm in a swollen state.

Evaluation of Characteristics of Sensor Material

Evaluation of the characteristics was performed on thus prepared sensor material (stimulus-responsive high polymer gel particles) according to a similar manner to Example 1. As a result, it was confirmed that when a glucose concentration in the added buffer solution was increased over 0 to 20 mM, a transmittance of the sensor material dispersion liquid significantly changed from 60% to 10%.

It has been known that Co(II)phthalocyanine pigment included in a sensor material decomposes glucose to reduce pH inside a sensor material. On the other hand, a stimulus-response high polymer gel constituting the sensor material has a nature that the high polymer gel shrinks with decrease in pH and a light absorption efficiency and others of the stimulus-response high polymer gel decreases in company with the shrinking.

Therefore, an observed change in transmittance is considered as a result of a phenomena that by addition of glucose, pH inside the sensor material decreases and thereby the stimulus-responsive high polymer gel shrinks to reduce a light absorption efficiency and others thereof, so a transmittance of the sensor material dispersion liquid increases.

Accordingly, the sensor material of Example 6 was found to be a high sensitivity sensor material that a transmittance significantly changed in a low glucose concentration region by swelling or shrinking of the stimulus-responsive high polymer gel constituting the sensor material.

Comparative Example 1

Preparation of Sensor Material and Evaluation of Characteristics of Sensor Material A high polymer gel particles including glucose oxidase was prepared by excluding phthalocyanine blue pigment from Example 1 to perform similar evaluation. Although a small change in transmittance from 60% to 59% in company with swelling and shrinking was confirmed, no large change in optical density (a change in transmittance) as in Example 1 was seen.

Fabrication of Sensor and Evaluation of Characteristics

A sensor was fabricated using thus prepared sensor material (high polymer gel particles including glucose oxidase) in a similar manner to Example 1 and evaluation of characteristics of the sensor was performed.

In a high glucose concentration, shrinking of the high polymer gel particles including glucose oxidase was conspicuous and a change in optical density was observed. However, in a low glucose concentration, no change in optical density (a change in transmittance) was detected and therefore, no correlation was confirmed between a glucose concentration and an optical density.

Comparative Example 2

Preparation of Sensor Material and Evaluation of Characteristics of Sensor Material A high polymer gel particles including urease was prepared by excluding phthalocyanine blue capsule pigment from Example 5 to perform similar evaluation to Example 5. Although a small change in transmittance from 70% to 68% in company with selling and shrinking was confirmed, no large change in optical density (a change in transmittance) as in Example 5 was confirmed.

Fabrication of Sensor and Evaluation of Characteristics

A sensor was fabricated using thus prepared sensor material (high polymer gel particles including urease) and evaluation of characteristics of the sensor was performed.

In a high urea concentration, shrinking of the high polymer gel particles including urease was conspicuous and a change in optical density was observed. However, in a low glucose concentration, no change in optical density (a change in transmittance) was detected.

A sensor material of the present invention using a stimulus-responsive high polymer gel including a bio-substance-responsive material such as an enzyme specifically reacting with a bio-substance and, for example, performing a change in optical characteristic due to an enzymatic reaction requires no measuring apparatus; therefore, there can be realized a sensor with a simple construction and at the same time, high general versatility.

The entire disclosure of Japanese Patent Application No. 2000-371234 filed on Dec. 6, 2000 including specification, claims, drawings and abstract is incorporated herein by reference in its entirety.

What is claimed is:

1. A sensor material comprising at least a stimulus-responsive high polymer gel, a bio-substance-responsive material, and a colored pigment.

2. The sensor material according to claim 1, wherein at least the bio-substance-responsive material and the colored pigment are present inside the stimulus-responsive high polymer gel.

3. The sensor material according to claim 1, wherein the colored pigment is present inside the stimulus-responsive high polymer gel while the bio-substance-responsive material is present outside the stimulus-responsive high polymer gel.

4. The sensor material according to claim 1, wherein the stimulus-responsive high polymer gel swells or shrinks according to a concentration of the bio-substance.

5. The sensor material according to claim 1, wherein a concentration of the colored pigment included in the stimulus-responsive high polymer gel is equal to or higher than a saturated absorption concentration or a saturated scattering concentration when the stimulus-responsive high polymer gel shrinks.

6. The sensor material according to claim 1, wherein a ratio of a volume of the stimulus-responsive high polymer gel in swelling state to a volume of the stimulus-responsive high polymer gel in shrinking state is 5 or more.

7. A sensor comprising at least the sensor material according to claim 1 and an optical waveguide.

8. A detection method for a bio-substance using the sensor material according to claim 1, comprising the step of detecting a change in tone on the basis of swelling or shrinking of the stimulus-responsive high polymer gel.

9. A detection method for a bio-substance using the sensor material according to claim 1, comprising the step of detecting a transmitting light therethrough on the basis of swelling or shrinking of the stimulus-responsive high polymer gel.

* * * * *